United States Patent [19]

McClure

[11] 4,399,288

[45] Aug. 16, 1983

[54] SEPARATION OF A 2-OXAZOLINE FROM AN AQUEOUS SOLUTION

[75] Inventor: John C. McClure, Midland, Mich.

[73] Assignee: The Dow Chemical Company, Midland, Mich.

[21] Appl. No.: 226,971

[22] Filed: Jan. 21, 1981

[51] Int. Cl.$^3$ ............................................ C07D 211/34
[52] U.S. Cl. .................................. 548/239; 210/640; 210/651
[58] Field of Search ................ 548/239; 210/640, 651; 55/16, 58

[56] References Cited

U.S. PATENT DOCUMENTS

| | | | |
|---|---|---|---|
| 2,953,502 | 9/1960 | Binning et al. | 210/640 |
| 2,981,680 | 4/1961 | Binning et al. | 210/23 |
| 3,225,107 | 12/1965 | Kirkland et al. | 260/252 |
| 3,402,107 | 9/1968 | Seelinger et al. | 203/14 |
| 4,082,658 | 4/1978 | Fritzsche et al. | 210/640 |
| 4,218,312 | 8/1980 | Perry | 210/640 |

FOREIGN PATENT DOCUMENTS 1502562 3/1978 United Kingdom .

OTHER PUBLICATIONS

Aptel, P. et al., Chemical Abstracts, vol. 85, 1976, 167417h.
Elderfield, R., "Heterocyclic Compounds", 1957, p. 324, vol. 5.

Primary Examiner—Donald G. Daus
Assistant Examiner—S. A. Gibson
Attorney, Agent, or Firm—Charles J. Enright

[57] ABSTRACT

A 2-oxazoline is separated from an aqueous solution by contacting this solution with a membrane selectively permeable to the 2-oxazoline, removing the 2-oxazoline as a vapor on the other side of the membrane and recovering it by cooling. Polyethylene hollow fibers are particularly desirable membranes, which purify the 2-oxazoline as it is separated from the water.

9 Claims, No Drawings

SEPARATION OF A 2-OXAZOLINE FROM AN AQUEOUS SOLUTION

BACKGROUND OF THE INVENTION

This invention relates to a process for separating a 2-oxazoline from an aqueous solution. More specifically, this invention employs a selectively permeable membrane to separate the oxazoline.

The art has long sought a method for the separation of a 2-oxazoline from an aqueous solution. However, the methods taught in the prior art suffer from one or more deficiencies.

It is recognized in U.S. Pat. No. 3,402,107 that the separation of water from a 2-oxazoline by distillation is difficult due to the formation of azeotropic mixtures of the oxazoline with water. These difficulties can be overcome by adding to the distillation mixture an organic solvent which forms an azeotrope with water, but this patented process is energy intensive.

British Pat. No. 1,502,562 describes a process for separating a weak base from an aqueous solution. In this process, the weak base permeates through a selectively permeable membrane to produce a concentrated solution of the base with a complexing agent on the other side of the membrane. Although 2-oxazolines are not enumerated as bases in this patent, these compounds are known to be weak bases. However, the 2-oxazolines would undergo hydrolysis in the presence of the acidic complexing agents employed in the reference process.

SUMMARY OF THE INVENTION

A process has been discovered for separating a 2-oxazoline, represented by the formula

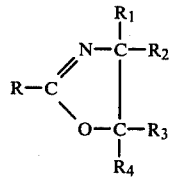

wherein $R_1$–$R_4$ are each independently hydrogen, $C_1$–$C_2$ alkyl or $C_1$–$C_2$ hydroxyalkyl and R is hydrogen, $C_1$–$C_4$ alkyl or $C_2$–$C_4$ alkenyl, from an aqueous solution. This process comprises the steps of (a) contacting an aqueous solution of a 2-oxazoline with a surface of a polymeric membrane, which is selectively permeable to the 2-oxazoline but not to water;

(b) permeating the 2-oxazoline through the membrane to a non-communicating permeate zone;

(c) transporting the 2-oxazoline from the permeate zone to a recovery zone; and (d) recovering the 2-oxazoline essentially free of water in the recovery zone.

DETAILED DESCRIPTION OF THE INVENTION

The 2-oxazolines of formula I are well-known compounds. General methods for the preparation of such 2-oxazolines are described by John A. Frump in *Chemical Reviews*, Vol. 71, No. 5, pp. 483-491. Preferably, $R_1$ and $R_2$ in formula I are each mmethyl or hydrogen and $R_3$ and $R_4$ are hydrogen. More preferably, $R_1$–$R_4$ are each hydrogen. R in formula I is preferably methyl or isopropenyl, more preferably ethyl.

In one preferred embodiment, a 2-alkyl-2-oxazoline is prepared by thermal dehydration of the corresponding N-2-hydroxyethyl derivative of an alkanoic acid in an aqueous solution. This dehydration reaction coproduces with the 2-oxazoline, water and minor impurities, such as amide adducts of the 2-oxazoline. Surprisingly, treatment of the resulting aqueous solution of the 2-oxazoline by the subject method results in the recovery of essentially pure 2-oxazoline.

Step (a)

Advantageously, the aqueous solution of 2-oxazoline employed as a feed in the subject process is present in the same aqueous solution in which it was prepared. The instant process works most efficiently with aqueous solutions containing at least about 1 percent 2-oxazoline, preferably about 30 to about 40 percent 2-oxazoline by weight. Solutions of lower concentration than is preferred are operable, but are advantageously first concentrated by distillation. In one embodiment, the aqueous 2-oxazoline is distilled and the resulting azeotropic mixture is employed as feed in the subject process.

The aqueous 2-oxazoline solution should contact a surface of the polymeric membrance at conditions which promote the selective permeation of the 2-oxazoline through the membrane. The rate of permeation is affected by numerous factors including the membrane material, the identity of the 2-oxazoline, the temperature, the concentration of the 2-oxazoline solution, pressure, and the rate at which the 2-oxazoline is removed from the non-communicating permeate zone.

Generally, the temperature during contact between the membrane and the oxazoline solution must be low enough to maintain the integrity of the polymer membrane during permeation, but high enough to promote permeation of the 2-oxazoline through the membrane. A temperature of from about 15° C. to about 100° C. is generally operable, with a temperature of about 40° C. to about 60° C. being preferred. Higher temperatures within the operable range afford more rapid permeation, but also undesirably increase the rate of hydrolysis of the oxazoline and increase the risk of rupturing the membrane.

The polymeric membranes employed in the subject process are non-porous, but are selectively permeable to 2-oxazoline compounds. These polymers must not be soluble in or react with the 2-oxazoline. For example, polyamides are generally soluble in or swell in 2-ethyl-2-oxazoline and are not suitable as membranes in the subject process. Homopolymers and copolymers of olefins, such as propylene and ethylene are preferred membrane materials. Surface-graft polymers, which are disclosed in U.S. Pat. No. 3,225,107, can also be used as membranes. Polyethylene membranes are particularly preferred. Surprisingly, many of these membranes not only effect separation of the 2-oxazoline from water, but also separation from impurities, such as the 2-oxazoline/amide adduct produced during preparation of the oxazoline.

The art concerning selectively permeable membranes is replete with disclosures concerning membrane support, membrane preparation, rate of fluid flow and other operating parameters. The subject process is conveniently practiced with conventional apparatus. This process can be practiced batchwise, but is advantageously performed in a continuous process. The skilled artisan can empirically determine the flow rate of the aqueous oxazoline, temperature, and other operating parameters which effect the optimal separation for a given membrane. The aqueous solution after contacting the membrane can be conveyed to additional membrane systems or recycled as necessary to effect additional recovery of the 2-oxazoline remaining in solution.

The polymeric membrane can be employed in any one of a number of possible configurations known to the art. This membrane can operably be a simple sheet mounted in a pipe. In one preferred embodiment, the membrane is deployed in hollow tubes or fibers through which or around which the aqueous oxazoline solution is circulated. It is critical that the membrane is free of holes and tears and is deployed so that the aqueous oxazoline solution is in contact with one of the membrane, but does not contact directly a second surface of the membrane. This second membrane surface defines a volume which the oxazoline can enter only by permeation through the membrane. This volume is referred to herein as a non-communicating permeate zone.

The membrane must be sufficiently thin to permit permeation, but thick enough not to rupture at the operating conditions of this process. Typically, the polymeric membrane can suitably be from about 0.002 to about 0.4 millimeter in thickness.

Steps (b) and (c)

The 2-oxazoline having permeated the membrane is desirably removed from the permeate zone, since presence of the 2-oxazoline in this zone will inhibit permeation of additional oxazoline. This removal may be conducted continuously or intermittently. Generally, the temperature of the permeate zone is essentially the same as that on the other side of the membrane. However, slightly higher temperatures can be employed in the permeate zone, so long as no disruption of the membrane occurs. Temperatures of from about 40° C. to about 100° C. are operable.

The vapor pressure of the 2-oxazoline is significant at normal operating temperatures. The 2-oxazoline can be conveniently removed from the permeate zone by maintaining a low pressure or vacuum to promote vaporization of the 2-oxazoline. Generally, a pressure differential across the membrane between the aqueous solution and the permeate zone of from about 50 to about 700 millimeters of mercury is advantageous to promote permeation and vaporization. The oxazoline vapors will naturally diffuse from the permeate zone to any communicating space. Alternatively, the oxazoline vapors can be swept from the permeate zone in a liquid or preferably a gas which is inert to and is readily separable from the 2-oxazoline. Dry nitrogen, carbon dioxide or air are preferred as sweep gases. Of course, liquids or gases which dissolve or have a deleterious effect on the membrane are not suitable.

Step (d)

The gaseous 2-oxazoline is readily recovered by cooling. Advantageously, a simple condenser can be employed to cool the 2-oxazoline to its condensation point. This recovery zone is desirably in close proximity to the permeate zone to minimize loss of 2-oxazoline during transport. The condenser can be cooled by conventional techniques. In one preferred embodiment of this invention, adiabatic expansion of the vapors is employed to assist in cooling.

Some minor amount of oxazoline is typically "lost" during the initial operation of the membrane and associated apparatus used in the subject process. However, after this initial "break-in period", recovery of 2-oxazoline is essentially quantitative based on the 2-oxazoline permeating the membrane.

The following examples illustrate the invention. All parts and percentages are by weight.

EXAMPLE 1

Through a bundle of polyethylene hollow fibers having a total cross-sectional area of 0.32 square feet and a length of 1 foot is pumped an aqueous solution of 2ethyl-2-oxazoline at a rate of from 20 to 50 milliliters per minute. The fibers are of conventional manufacture and have an average internal diameter of 200 microns. The fiber bundle is housed in a closely fitted shell. Dry nitrogen gas is purged at a rate of 0.2 to 0.5 standard cubic feet per minute through the shell, so as to sweep the outer surface of the fibers.

The composition of the aqueous oxazoline feed, as determined by gas chromatography, is initially 64 percent 2-ethyl-2-oxazoline, 33 percent water and 3 percent of an amide adduct of the oxazoline and other impurities. The temperature of this solution and fibers is maintained in the range from 40° C. to 50° C. The aqueous solution exiting from the fibers is returned to the aqueous oxazoline feed vessel.

The nitrogen gas exiting from the shell is passed to a condensing vessel, where the gas is cooled to a temperature of −50° C. 2 Grams of 2-ethyl-2-oxazoline are collected in this condenser in 4 hours. This 2-ethyl-2-oxazoline is found by conventional gas chromatographic analysis to contain less than 0.01 percent of the amide adduct and is essentially free of water, i.e., contains less than 5 percent water.

What is claimed is:

1. A process for the separation of a 2-oxazoline, represented by the formula I

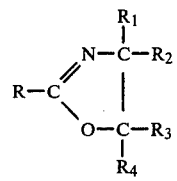

wherein $R_1$–$R_4$ are each independently hydrogen, $C_1$–$C_2$ alkyl or $C_1$–$C_2$ hydroxyalkyl and R is hydrogen, $C_1$–$C_4$ alkyl or $C_2$–$C_4$ alkenyl, from an aqueous solution, said process comprising the steps of (a) contacting an aqueous solution of a 2-oxazoline and an amide adduct of 2-oxazoline with a surface of a polymeric membrane, comprising a homopolymer or copolymer of an olefin, which is selectively permeable to the 2-oxazoline but is less permeable to water and the amide adduct;

(b) permeating the 2-oxazoline through the membrane to a non-communicating permeate zone;

(c) transporting the 2-oxazoline from the permeate zone to a recovery zone; and (d) recovering the 2-oxazoline essentially free of water in the recovery zone.

2. The process as described in claim 1 wherein $R_1$–$R_4$ are each hydrogen and R is methyl, ethyl or isopropenyl.

3. The process as described in claim 2 wherein R is ethyl.

4. The process as described in claim 1 wherein a pressure differential in the range from about 50 to about 700 millimeters of mercury is maintained between the first surface of the polymeric membrane and the permeate zone during Steps (a) and (b).

5. The process as described in claim 1 or 4 wherein the polymeric membrane is a polyethylene hollow fiber.

6. The process as described in claim 1 wherein the temperature of the aqueous solution in Step (a) is in the range from about 40° C. to about 60° C.

7. The process as described in claim 6 wherein the temperature in the permeate zone is in the range from about 40° C. to about 80° C.

8. The process as described in claim 1 wherein the 2-oxazoline is transported as a vapor in Step (c).

9. The process as described in claim 8 wherein an inert gas stream is used to transport the 2-oxazoline vapors in Step (c).

* * * * *

UNITED STATES PATENT AND TRADEMARK OFFICE
CERTIFICATE OF CORRECTION

PATENT NO. : 4,399,288
DATED : August 16, 1983
INVENTOR(S) : John C. McClure

It is certified that error appears in the above—identified patent and that said Letters Patent is hereby corrected as shown below:

Column 1, line 67, "are each mmethyl" should read -- are each methyl --.

Column 2, line 27, "polymeric membrance at" should read -- polymeric membrane at --.

Column 3, line 17, "with one of the mem-" should read -- with one surface of the mem- --.

Column 4, line 13, "solution of 2eth-" should read -- solution of 2-eth- --.

Signed and Sealed this

Thirty-first Day of July 1984

[SEAL]

Attest:

GERALD J. MOSSINGHOFF

Attesting Officer    Commissioner of Patents and Trademarks